United States Patent
McMichael et al.

(10) Patent No.: US 12,426,960 B2
(45) Date of Patent: *Sep. 30, 2025

(54) MEDICAL DEVICE POSITION NOTIFICATION SYSTEM

(71) Applicant: Avent, Inc., Alpharetta, GA (US)

(72) Inventors: Donald McMichael, Roswell, GA (US); Kelley R. Biehl, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/661,830

(22) Filed: May 13, 2024

(65) Prior Publication Data
US 2024/0293188 A1 Sep. 5, 2024

Related U.S. Application Data

(63) Continuation of application No. 16/526,038, filed on Jul. 30, 2019, now Pat. No. 12,011,228.

(51) Int. Cl.
| | |
|---|---|
| *A61B 34/20* | (2016.01) |
| *A61B 5/00* | (2006.01) |
| *A61B 5/06* | (2006.01) |
| *A61J 15/00* | (2006.01) |

(52) U.S. Cl.
CPC .............. *A61B 34/20* (2016.02); *A61B 5/065* (2013.01); *A61B 5/743* (2013.01); *A61J 15/0084* (2015.05)

(58) Field of Classification Search
CPC ........ A61B 5/14539; A61B 2034/2051; A61B 34/20; A61B 5/0538; A61B 5/065; A61B 5/14503; A61B 5/4238; A61B 5/4836; A61B 2010/0061; A61B 2034/2061; A61B 90/37; A61J 15/00; A61J 15/0003; A61J 15/0011; A61J 15/0015
See application file for complete search history.

(56) References Cited

U.S. PATENT DOCUMENTS

| | | | |
|---|---|---|---|
| 4,836,214 A | 6/1989 | Sramek | |
| 4,921,481 A | 5/1990 | Danis et al. | |
| 6,233,476 B1 | 5/2001 | Strommer et al. | |
| 6,334,064 B1 | 12/2001 | Fiddian-Green | |

(Continued)

FOREIGN PATENT DOCUMENTS

WO    WO 92/17150 A1    10/1992

OTHER PUBLICATIONS

International Search Report and Written Opinion for PCT/US2020/044183, dated Nov. 12, 2020, 14 pages.

*Primary Examiner* — Amelie R Davis
(74) *Attorney, Agent, or Firm* — Meunier Carlin & Curfman LLC

(57) ABSTRACT

A medical device position notification system including a medical device and at least one sensor associated with the medical device, a processor, and a display device. The medical device is configured to be inserted into an orifice of the patient. The sensor measures information related to the position of the medical device in the patient's body, and communicates the information with the processor in real-time. The display device is coupled to the processor and is configured to display a tracing path of the position of the medical device in real-time. The display device is further configured to display a notification of the position of the medical device within the patient's body, such as a notification alert that the medical device has deviated from a predetermined path.

19 Claims, 9 Drawing Sheets

(56) References Cited

U.S. PATENT DOCUMENTS

| | | |
|---|---|---|
| 6,357,447 B1 | 3/2002 | Swanson et al. |
| 7,818,155 B2 | 10/2010 | Stuebe et al. |
| 8,147,486 B2 | 4/2012 | Honour et al. |
| 8,613,702 B2 | 12/2013 | Feer et al. |
| 8,986,230 B2 | 3/2015 | Nishtala |
| 9,114,226 B1 | 8/2015 | Lash et al. |
| 9,179,971 B2 | 11/2015 | Kirschenman |
| 9,226,878 B2 | 1/2016 | Elia et al. |
| 9,295,395 B2 | 3/2016 | Elia et al. |
| 9,532,739 B2 | 1/2017 | Bennett-Guerrero |
| 9,610,227 B2 | 4/2017 | Elia |
| 9,642,779 B2 | 5/2017 | Elia et al. |
| 9,713,579 B2 | 7/2017 | Elia et al. |
| 11,154,379 B2 | 10/2021 | Bothorel et al. |
| 2004/0087877 A1 | 5/2004 | Besz et al. |
| 2008/0097179 A1 | 4/2008 | Russo |
| 2008/0167607 A1 | 7/2008 | Pfeiffer et al. |
| 2008/0249467 A1 | 10/2008 | Burnett et al. |
| 2012/0016256 A1 | 1/2012 | Mabary et al. |
| 2012/0277619 A1 | 11/2012 | Starkebaum et al. |
| 2013/0225946 A1 | 8/2013 | Feer et al. |
| 2016/0005220 A1 | 1/2016 | Weingarten et al. |
| 2016/0113843 A1 | 4/2016 | Elia et al. |
| 2016/0129223 A1 | 5/2016 | Kirschenman |
| 2016/0324598 A1 | 11/2016 | Bothorel et al. |
| 2016/0331298 A1 | 11/2016 | Burnett et al. |
| 2017/0071502 A1 | 3/2017 | Bennett-Guerrero |
| 2017/0202750 A1 | 7/2017 | Elia |
| 2018/0078195 A1 | 3/2018 | Sutaria et al. |
| 2018/0092698 A1 | 4/2018 | Chopra et al. |
| 2018/0117285 A1 | 5/2018 | Shaughnessy et al. |
| 2018/0161249 A1 | 6/2018 | Elia et al. |
| 2018/0289536 A1 | 10/2018 | Burnett |
| 2019/0117519 A1 | 4/2019 | Schmid-Schonbein et al. |

MEDICAL DEVICE POSITION NOTIFICATION SYSTEM

CROSS-REFERENCE TO RELATED APPLICATIONS

The present application is a continuation of U.S. patent application Ser. No. 16/526,038 filed on Jul. 30, 2019, which is incorporated herein in its entirety by reference thereto.

FIELD OF THE INVENTION

The subject matter of the present invention relates generally to a system and method for notification of the position of a medical device within the body.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag delivers liquid nutrient, liquid medicine or a combination of the two to the patient.

Other types of catheters are inserted into the patient's veins or arteries for treating the cardiovascular system. These intravascular catheters include, among others, central venous catheters, peripheral venous catheters and the peripherally inserted central catheters. These catheters include a relatively small tube that passes through the patient's veins or arteries. Depending on the application, the health care provider can use an intravascular catheter to remove blood vessel blockages, place inserts into blood vessels and provide patients with injections of medications, drugs, fluids, nutrients, or blood products over a period of time, sometimes several weeks or more.

When using these known enteral and intravascular catheters, it is important to place the end of the catheter at the proper location within the human body. Erroneous placement of the catheter tip may injure or harm the patient. For example, if the health care provider erroneously places an enteral catheter into the patient's trachea, lungs, or other regions of the respiratory system rather than through the esophagus and to the stomach to reach the desired location in the digestive tract for delivering nutrients or medicine, liquid may be introduced into the lungs with harmful, and even fatal, consequences. In particular, the esophagus of the digestive tract and the trachea of the respiratory system are in close proximity to each other and are blind to the health care provider during catheter placement, which creates a dangerous risk for erroneous catheter placement. If the health care provider erroneously places an intravascular catheter into the wrong blood vessel of the cardiovascular system, the patient may experience infection, injury or a harmful blockage.

In some cases, health care providers use X-ray machines to gather information about the location of catheters within the body. There are several disadvantages with using X-ray machines. For example, these machines are relatively large and heavy, consume a relatively large amount of energy and expose the patient to a relatively high degree of X-ray radiation. Also, these machines are typically not readily accessible for use because, due to their size, they are usually installed in a special X-ray room. This room can be far away from the patient's room. Therefore, health care providers can find it inconvenient to use these machines for performing catheter insertion procedures. Moreover, even X-rays are not necessarily conclusive as to the location of the catheter tip, as the natural and continuous movement of the internal organs can make it difficult for the physician interpreting the X-ray to be sure of the actual location of the distal end of the catheter. In addition, using X-ray technology is expensive and is a time-consuming task that can create unnecessary delays in delivering critical nutrients to the patient.

Another existing catheter locating means involves using an electromagnetic coil positioned inside the catheter and an electromagnetic coil locating receiver outside of the patient's body. The electromagnetic coil is generally incorporated into a stylet or guide wire which is inserted within the catheter. The coil locating receiver can be used to determine the distance the coil is from the receiver and its depth in the patient's body and can communicate with a display to show a reference image of a non-subject body and an image of the coil located on the display with the reference image. However, these systems also have several disadvantages. For example, the coil locating receiver is a large device that must rest in a precise location outside the patient's body and does not permit for adjustments due to each individual patient's anatomical size or shape. However, a patient undergoing a feeding tube placement will be agitated and sudden movements are expected, which can move the coil locating receiver, thus increasing the likelihood of positional errors or complications in locating the catheter. Additionally, these existing systems can only display the coil location over a reference image of a non-subject (i.e., a generic patient) body without reference to the individual patient's particular anatomy. Thus, these existing systems can only generate generic warnings or alerts when a deviation from an intended path within the body is estimated. Such generic warnings or alerts are easily ignored by a health care provider because they provide little specific, actual information regarding the position of the catheter and do not adequately capture a health care provider's attention. Therefore, health care providers can estimate the positioning of the catheter using the electromagnetic coil and coil locating receiver but cannot estimate or view the specific patient's anatomy.

Consequently, there is a need for a system for notifying a user of the positioning of a medical device within a patient's body in real-time to ensure more accurate catheter placement. In particular, a notification system that provides a visual deviation alert when the medical device is improperly positioned would also be useful.

SUMMARY

The present invention is directed to a medical device position notification system. The system includes a processor; a display device; a medical device configured to be inserted into a patient's body; and at least one sensor associated with the medical device. The sensor communicates with the processor via an electrical connection to deliver signals from the sensor containing information relating to a position of the medical device within a patient's body measured by the at least one sensor to the processor in real-time. The display device is coupled to the processor and is configured to display a tracing path of the position of the medical device in real-time. The display device is configured to display a notification of the position of the medical device within the patient's body.

In one particular embodiment, the medical device position notification system can further include memory device storing instructions which, when executed by the processor, cause the processor to: (i) interpret the signals communicated by the at least one sensor, and (ii) cause the display device to communicate whether the position of the medical device has reached a predetermined position or deviated from a digestive tract of the patient based on the interpretation of the signals communicated by the at least one sensor.

In another embodiment, the at least one sensor can include a position sensor, a carbon dioxide sensor, a vacuum decay sensor, a light sensor, a sound sensor, a pressure sensor, a pH sensor, a humidity sensor, a temperature sensor, or a combination thereof.

In one more embodiment, the at least one sensor can include a first sensor and one or more second sensors, further wherein when the signals of the first sensor are interpreted to indicate that the position of the medical device has deviated from a digestive tract of the patient, signals from the one or more second sensors are provided to the processor and interpreted by the processor to confirm the position of the medical device. Moreover, the first sensor may be a position sensor and the one or more second sensors can include a carbon dioxide sensor, a vacuum decay sensor, a light sensor, a sound sensor, a pressure sensor, a pH sensor, a humidity sensor, a temperature sensor, or a combination thereof.

In an additional embodiment, the notification displayed on the display device is an illuminated visual symbol.

In still another embodiment, the notification displayed on the display device is a visual symbol in the shape of an organ. Further, the notification can be a visual symbol that is depicted as an image or outline of a right lung when the signals indicate that the medical device is in a right lung of the patient's body. Moreover, the notification can be a visual symbol that is depicted as an image or outline of a left lung when the signals indicate that the medical device is in a left lung of the patient's body. Further, the notification can be a visual symbol that is depicted as an image or outline of a stomach when the signals indicate that the medical device is in a stomach of the patient's body. Additionally, the notification is a visual symbol that can be depicted as an image or outline of a duodenum when the signals indicate that the medical device is in a small intestine of the patient's body.

In one more embodiment, the notification is displayed when the position of the medical device reaches a predetermined position or when the position of the medical device deviates from a predetermined path. Further, the notification displayed on the displayed device can light up a first warning color when a first sensor indicates that the medical device has deviated from the predetermined path. Moreover, the at least one sensor can include a first sensor and one or more second sensors, further wherein the notification displayed on the display device changes from the first warning color to a second warning color when at least one of the one or more second sensors confirms the first sensor indication that the medical device has deviated from the predetermined path. Additionally, the predetermined path can be along a midline of the patient. Further, the display device can display a notification of the position of the medical device within the patient's body when the position of the medical device deviates to the right or left of the midline.

In an additional embodiment, the notification displayed on the displayed device can be a first confirmation color when the at least one sensor indicates that the medical device has reached a predetermined position.

In a further embodiment, the notification displayed on the display device is a flashing visual symbol.

The present invention is further directed to a method for medical device position guidance. The method includes steps of: providing a medical device configured to be inserted into the body and at least one sensor associated with the medical device; inserting the medical device into an orifice of the body; electrically connecting the sensor to a processor via a wired connection or a wireless connection; activating the at least one sensor, wherein the at least one sensor measures information relating to the position of the medical device within a patient's body and sends signals containing the information relating to the position of the medical device within the patient's body to the processor via the wired or wireless electrical connection in real-time, wherein a display device is coupled to the processor and displays the position of the medical device within the patient's body communicated by the sensor; advancing the medical device inside the body in a direction away from the orifice while the at least one sensor is activated; and observing the position of the medical device within the patient's body on the display device, wherein the display device is configured to display a notification of the position of the medical device within the patient's body.

In one particular embodiment of the method, a memory device stores instructions which, when executed by the processor, cause the processor to: (i) interpret the signals communicated by the at least one sensor, and (ii) cause the display device to communicate whether the position of the medical device has reached a predetermined position and/or deviated from the digestive tract of the patient based on the interpretation of the signals communicated by the at least one sensor.

In another embodiment, the orifice can be a nose or a mouth.

In an additional embodiment, the notification of the position of the medical device within the patient's body is displayed when the medical device deviates from the digestive tract. Further, the notification of the position of the medical device within the patient's body can be displayed when the signals from the at least one sensor indicate that the medical device enters the trachea and/or lungs.

In one more embodiment, the notification displayed on the display device is a visual symbol in the shape of an organ.

In still another embodiment, the at least one sensor comprises a first sensor and one or more second sensors, the method further including the step of providing signals from the one or more second sensors to the processor and interpreted by the processor to confirm the position of the medical device when the signals of the first sensor are interpreted by the processor to indicate that the position of the medical device has deviated from a digestive tract of the patient. Further, the first sensor can be a position sensor and the one or more second sensors can include a carbon dioxide sensor, a vacuum decay sensor, a light sensor, a sound sensor, a pressure sensor, a pH sensor, a humidity sensor, a temperature sensor, or a combination thereof.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
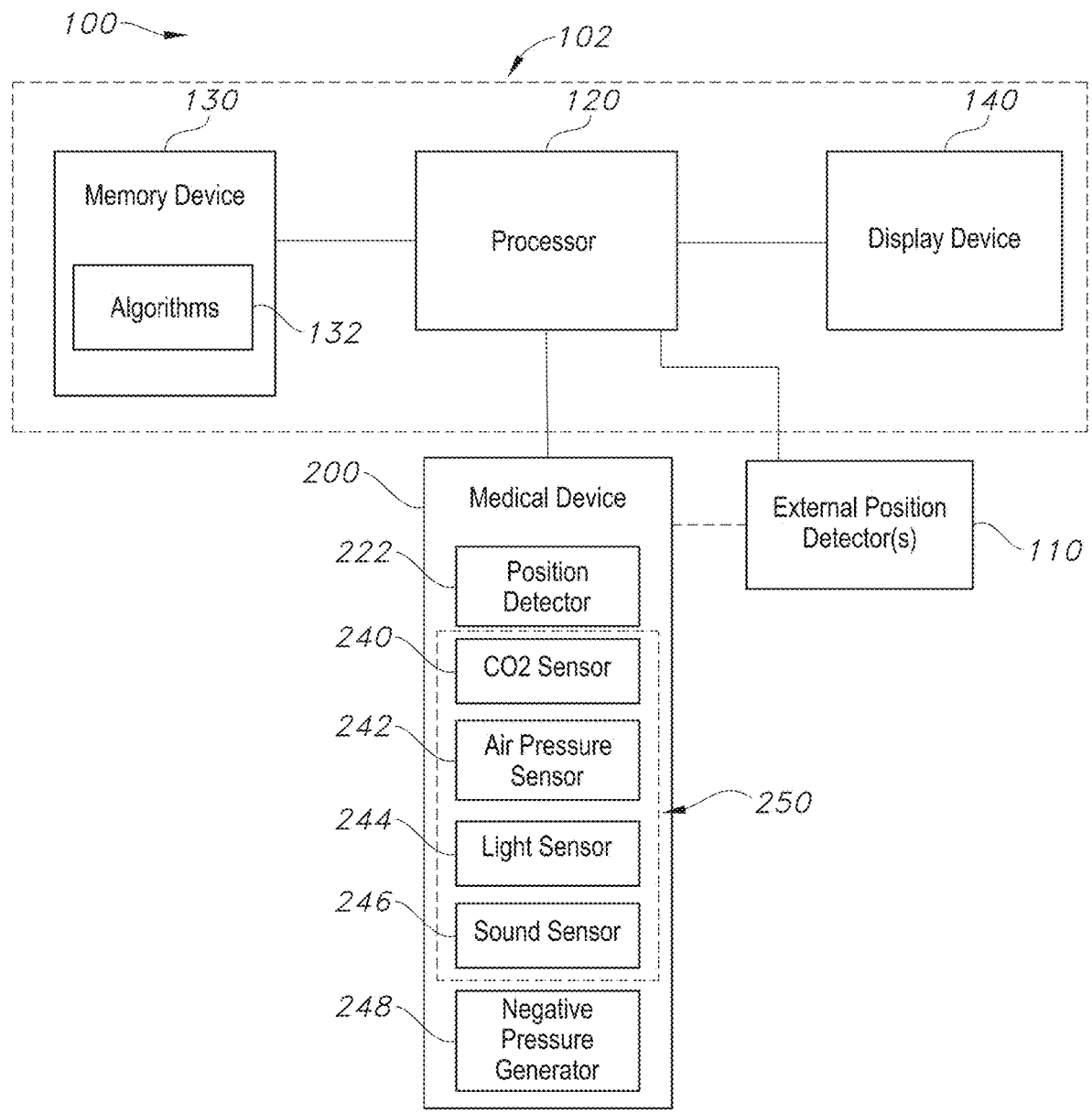
FIG. 1 illustrates a schematic block diagram of the medical device position notification system according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

As used herein, the term "in-scale" indicates an article or image that is in proportion to its surroundings, with all parts accurately sized and proportioned in relation to each other.

Generally speaking, the present invention is directed to medical device position notification system that includes a processor, a display device, a medical device configured to be inserted into a patient's body, and at least one sensor associated with the medical device. The sensor communicates with the processor via an electrical connection to deliver signals from the sensor containing information relating to the position of the medical device within a patient's body measured by the at least one sensor to the processor in real-time. The display device is coupled to the processor and is configured to display a tracing path of the position of the medical device in real-time. Further, the display device is configured to display a notification of the position of the medical device within the patient's body. The present inventors have found that the medical device position notification system and method described in more detail herein provides superior notifications, in the form of warning alerts and/or position confirmation notifications, regarding the placement of a medical device that is inserted within a patient's body. Particularly, the system of the present invention implements one or more sensors that measure information related to the position of the medical device within the patient's body to confirm the position of the medical device. The use of more than one type of sensor, as described herein, can confirm the position information interpreted from each of the different sensors. In addition, the present inventors have found that an anatomy-shaped visual notification symbol displayed in-scale with the patient's anatomy on the display device provides superior feedback to a health care provider regarding the position of the medical device that is less likely to be ignored than a black-and-white and/or not-to-scale generic alert on a display screen. The specific features of the medical device position notification system of the present invention may be better understood with reference to FIGS. 1-10.

Referring now to FIG. 1, a medical device position notification system 100 contemplated by the present invention includes: a housing 102 surrounding a control unit or processor 120 coupled to a memory device 130 and a display device 140; a medical device 200; and at least one sensor that is configured to deliver signals to the processor 120 regarding the position of the medical device 200. The system 100 can also include an external position detector 110 configured to detect the anatomical shape and size of the patient. The external position detector 110 can be coupled to the processor 120 through a wired or wireless connection. The at least one sensor can additionally include one or more sensors associated with the medical device 200. For example, the medical device 200 can include one or more of a position detector such as a signal generator 222, a carbon dioxide ($CO_2$) sensor 240, an air pressure sensor 242, a light sensor 244, a sound sensor 246, a humidity sensor, a temperature sensor, or combinations thereof. The sensor(s) can continuously sense information regarding the position of the medical device 200 in real-time. The memory device 130 includes machine readable instructions and one or more computer programs (which, for example, may include a plurality of algorithms 132) which are used by the processor 120 to process the signal data produced by the sensor(s). The display device 140 is configured to indicate information regarding the position of the medical device 200 to the health care provider, such as in the form of a visual symbol 150 on a display 142 (see FIGS. 8-10). The display device 140 may be any suitable display mechanism including, but not limited to, a liquid crystal display (LCD), light-emitting diode (LED) display, cathode-ray tube display (CRT), or plasma screen.

Figure 2:
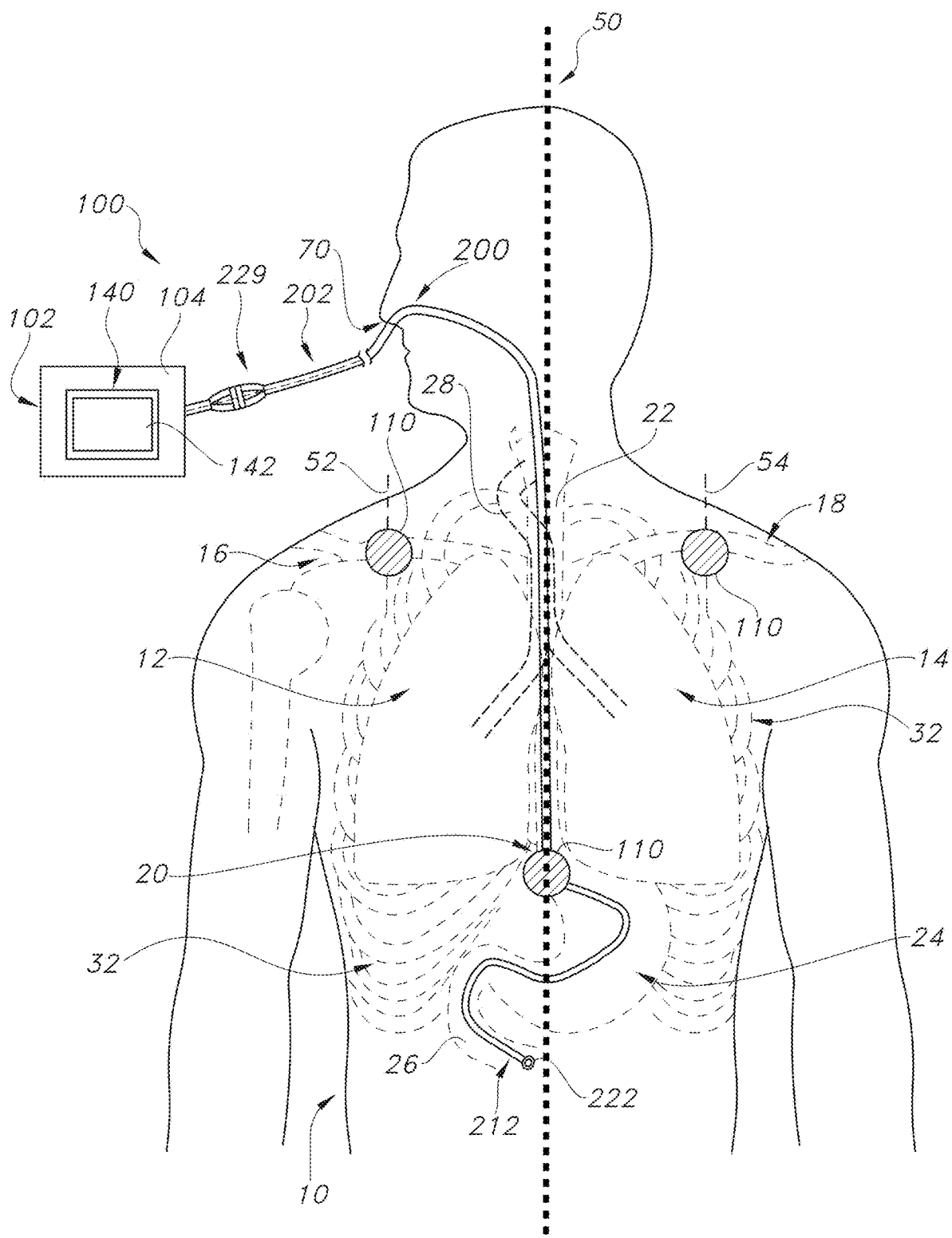
FIG. 2 illustrates a predetermined arrangement of external position detectors according to one embodiment of the medical device position notification system of FIG. 1.

Health care providers can use the system 100 in a variety of implantable medical device, e.g., catheter, applications. In one application illustrated in FIG. 2, the system 100 is used in an enteral application. Here, a portion of the medical device 200, in this case an enteral catheter, is placed through an orifice 70 of the patient, such as the patient's nose or mouth. The distal end or tip 212 of the medical device 200 can ultimately be positioned in the stomach 24 or the small intestine 26. However, misplacement of the distal tip 212 in the patient's respiratory tract, e.g., the trachea, bronchi, or lungs, rather than in the patient's gastrointestinal tract is a complication of insertion of enteral catheters due to the bifurcation of the esophagus 22 and the trachea 28 as shown in FIG. 2. It is known that the bifurcation of the esophagus 22 and the trachea 28, as illustrated in FIG. 2, occurs at a certain distance from the entrance to the nostril in a patient 10, with the certain distance varying between pediatric and adult patients. Knowing this distance for a given patient, as well as the length of the enteral catheter tube 210, the user can determine how much (or what length) of the tube 210 has been inserted into the patient and, thus, know whether the distal tip 212 of the tube 210 is at or near the point where the trachea branches off from the digestive tract, from which the tube 210 could be misplaced into the patient's airway. As an example, bifurcation typically occurs around 18-20 cm from the entrance to the nostril in adults; the area where bifurcation occurs may be referred to as a bifurcation zone.

As the health care provider advances the medical device 200 towards the patient's stomach 24, the sensor(s) can continuously monitor various biometric data relating to the position of the medical device 200 within the patient's body 10. The display device 140 can indicate information related to the position of the distal tip 212 within the body 10 as well as information related to the shape of the pathway taken by the distal tip 212 through the body 10. For example, as will be described in further detail below, a signal generator 222 of the medical device 200 can be in operative communication with the at least one external position detector 110, e.g., three distributed external position detectors 110 as shown in FIG. 2, to determine the position of the signal generator 222 in terms of relative X, Y, Z coordinates. It should be appreciated that the system 100 need not indicate the precise location or path of the medical device 200 to provide assistance to the health care provider.

The three distributed external position detectors 110 can be positioned in a predetermined arrangement on the external anatomy of the patient 10. The predetermined arrangement of the external detector devices 110 can include multiple predetermined external fixation points on the subject's external anatomy, where each of the predetermined external fixation points are distributed or separated from each other as shown in FIG. 2. The predetermined external fixation points can be based on well-known external anatomical landmarks. In some embodiments, the well-known external anatomical landmarks can be bony landmarks, as the bony landmarks can be located visually or palpated on subjects of any shape or size regardless of physical presentation of the subject, such as the presence of adipose tissue, edema, or other tissues.

For example, as illustrated in FIG. 2, when the medical device position notification system 100 is used to determine positioning of a medical device 200 within a subject's upper anatomy such as for inserting an enteral catheter (feeding tube), three external detector devices 110 can be positioned on the subject 10. For instance, one device 110 can be placed at a right upper landmark, such as the right midclavicular line 52, one device 110 can be placed at a left upper landmark, such as the left midclavicular line 54, and one device 110 can be placed at a central landmark, such as the xiphoid process 20. As illustrated in FIG. 2, the xiphoid process 20 is the cartilaginous section at the lower end of the sternum 30 which is generally positioned along the mid-sagittal line 50 and which is not attached to any ribs 32 and is gradually ossified in adult humans. The right and left midclavicular lines 52 and 54 are each imaginary lines which are generally parallel to the mid-sagittal line 50 and pass downwards over the trunk of the human body 10 through the midpoint of the right and left clavicle bones 16 and 18, respectively. However, the midclavicular lines 52 and 54 and the xyphoid xiphoid process 20 are not the only landmarks that could be used for this purpose. There may be other points of the body to which the predetermined arrangement of the plurality of external detector devices 110 could be reliably co-located or located with a predetermined offset for use in a reliable position guidance system.

In general, and referring to FIGS. 2, 3A-C and 4, the plurality of external detector devices 110 each include a housing 112 which supports a signal receiver 180 operably coupled to the processor 120. According to the embodiment, the medical device position notification system 100 is operable to provide audiovisual information about the shape, size, and orientation of a subject's anatomy through a wired or wireless connection between the plurality of external detector devices 110 and the processor 120 on the display device 140.

Figure 3A:
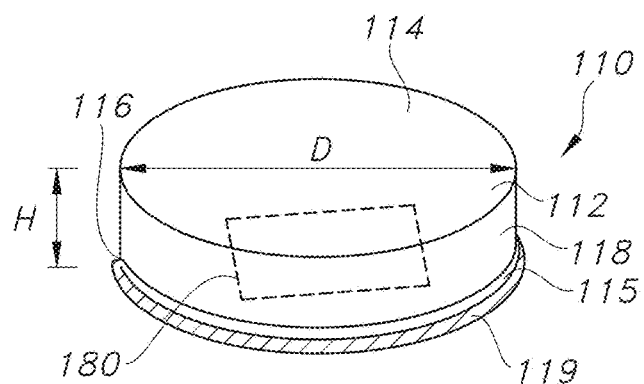
FIG. 3A illustrates a perspective view of a housing of an external position detector of the medical device position notification system of the present invention.

As illustrated in FIGS. 3A-C and 4, each of the external detector devices 110 includes a housing 112 surrounding a signal receiver 180. The housing 112 can include an upper surface 114, a lower surface 116, and at least one side surface 118 extending from the upper surface to the lower surface. For example, as shown in FIG. 3A, the upper surface 114 and the lower surface 116 can be circular or oval in shape and have a continuous side surface 118 extending therebetween, forming a generally cylindrical-shaped housing 112. In another embodiment (not shown), the upper surface 114 and the lower surface 116 can be rectangular in shape and can have four side surfaces 118 extending therebetween corresponding to each of the sides of the rectangle. However, the external shape of the housing 112 of each external detector device 110 is of little consequence to the way in which the actual signal receiver 180 works. As such, the housing 112 can have any other suitable external shape based on a particular application of the medical device position notification system 100.

The housing 112 of each external detector device 110 can have a footprint (i.e., shape and size of the lower surface 116) that is generally comparable to standard electrocardiogram leads. For example, the housing 112 can have a diameter D extending across the widest portion of the upper surface 114 or lower surface 116 that is in a range from about 0.5 inches (1.25 cm) to about 5 inches (13 cm), or any value or range therebetween, such as from about 1 inch (2.5 cm) to about 3 inches (7.6 cm), for example from about 1.5 inches (3.8 cm) to about 2.5 inches (6.4 cm). The at least one side surface 118 of the housing 112 can have a height H in a range from about 0.25 inches (0.63 cm) to about 2 inches (5.1 cm), or any value or range therebetween, such as from 0.3 inches (0.76 cm) to about 1 inch (2.5 cm), for example about 0.5 inches (1.25 cm). In addition, each of the external detector devices 110 can be lightweight.

Figure 3B:
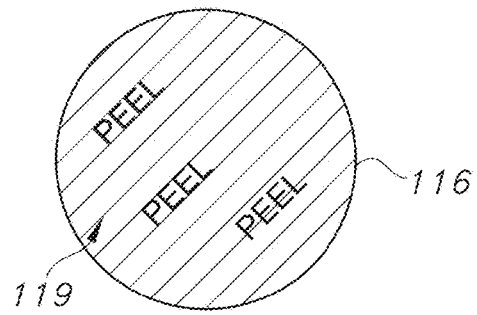
FIGS. 3B-C illustrate bottom views of the housing of FIG. 3A.
Figure 3C:
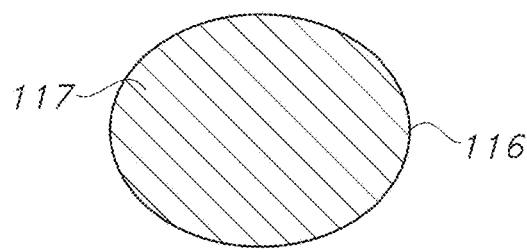

As shown in FIGS. 3A-C, each external detector device 110 can further include a fixation mechanism 115 that is configured to affix the external detector device 110 to the subject. In a preferred embodiment, the external detector device 110 can be directly affixed to the subject's body 10 by the fixation mechanism 115 so that the external detector device 110 maintains a fixed reference point in relation to the subject 10. Thus, when the subject 10 moves, the external detector device 110 moves with the subject 10 to maintain a static frame of reference with respect to the particular patient. The fixation mechanism 115 can be positioned on the lower surface 116 of the external detector device housing 112. For example, the fixation mechanism 115 can include an adhesive material 117 that is configured to affix the external detector device 110 to the skin of the subject, a patch on the subject's body, or a garment worn by the subject. The adhesive material 117 can be an adhesive substrate that can be adhesive on both sides such that it adheres to the lower surface 116 of the housing 112 on one side and to a subject's body or garment on the other side. When the fixation mechanism 115 is adhesive material 117 adhered to the lower surface 118 of the housing 112, the external detector device 110 can additionally include a peelable protective sheet 119 covering the entire adhesive material 117. The peelable protective sheet 119 can be removed prior to affixing the adhesive 117 to the subject 10 or the subject's garment. Optionally, a used adhesive substrate 117 can be removed from the housing 112 and discarded, and a new adhesive substrate 117 can be applied. Alternatively, the adhesive material 117 can be any suitable adhesive arrangement which is capable of releasably adhering the housing 112 to the subject's skin or garment. In other embodiments, the fixation mechanism 115 can include a clip, pin, magnet, hook and loop system, or any other suitable means for affixing the external detector device 110 to a subject's body or garment. By using a fixation mechanism 115 on each external detector device 110 that can affix the external detector device 110 to the subject's body or garment, the frame of reference of each external detector device 110 can remain stationary with the subject's body. Thus, the likelihood of positional errors when using the medical device position guidance system 100 can be reduced as compared to other guidance systems because there can be fewer complications arising due to movement of the subject's body.

Figure 4:
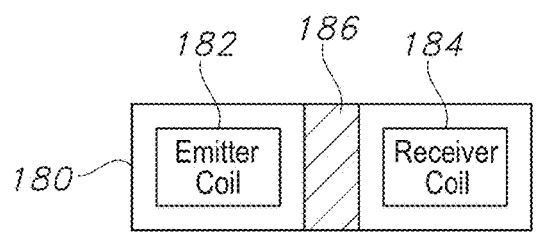
FIG. 4 illustrates an emitter/receiver of the external position detector of FIG. 3A.

As illustrated in FIGS. 3A and 4, each external detector device 110 can include a signal receiver 180. In one embodiment, each external detector device 110 may include an electromagnetic emitter 182 formed through a plurality of coils of wire(s) connected to a power source (not shown). The power source can be a wired or wireless connection to a power source within the housing 102 or can be a battery within the external detector device 110. When the power source sends electrical current to the emitter coils, the emitter coils can transmit a signal or electromagnetic field capable of being detected by an electromagnetic receiver 184. Although the emitter coils are disclosed as one example of a magnetic field emitter, it should be appreciated that the electromagnetic emitter 182 can include any suitable mechanism or device which generates or produces detectable electromagnetic energy or a magnetic field, such as a permanent magnet, resistive magnet, or superconducting magnet.

As shown in FIGS. 3A and 4, each external detector device 110 can include a signal receiver 180 having an electromagnetic receiver 184 that can detect an electromagnetic field or signal generated by an electromagnetic emitter 182, such as the electromagnetic emitters 182 of the other external detector devices 110 and/or the signal generator 222 of the medical device 200. The electromagnetic receivers 184 can each include at least one receiver coil, such as three receiver coils, that are operable to receive an induced current and detect the induced voltage in response to a magnetic field generated by an electromagnetic field emitter 182 when the magnetic field is directed toward and reaches the receiver coil(s). It should be appreciated that the receiver coils may be any suitable structures capable of receiving an induced current in response to a generated magnetic field. In some embodiments, each of the plurality of external detector devices 110 can include both an electromagnetic emitter 182 and an electromagnetic receiver 184 as part of the signal receiver 180. Additionally, there can be shielding 186 within signal receiver 180 between the electromagnetic emitter 182 and the electromagnetic receiver 184. The shielding 186 can prevent signal interference between the electromagnetic emitter 182 and the electromagnetic receiver 184 within the signal receiver 180. For example, the shielding 186 can be a barrier between the electromagnetic emitter 182 and the electromagnetic receiver 184 that can be made of conductive or magnetic materials.

When the plurality of external detector devices 110 are positioned in the predetermined arrangement on the subject 10 based on predetermined external landmarks, the locations of the landmarks can provide adequate separation of the external detector devices 110 on the subject to enable the electromagnetic emitters 182 and receivers 184 of each external detector device 110 to interrogate each other, i.e., for the emitters 182 to emit an electromagnetic field and for the receivers 184 detect the magnetic fields emitted by the respective emitters 182 of the other external detector devices 110. Each external detector device 110 can send one or more signals to the processor 120 detailing the detected coil voltage of the receivers 184. Each external detector device 110 can also send one or more signals to the processor 120 detailing the drive signals used to generate the electromagnetic fields with the emitters 182. The processor 120 can compare each of the detected coil voltages and the drive signals used to create the electromagnetic fields to assess and calculate the distance and the relative angular orientation between each of the receivers 184 of the external detector devices 110 to define an electromagnetic three-dimensional volume. Using algorithms 132 stored in the memory 130, the processor 120 can use data collected about the electromagnetic three-dimensional volume to derive the subject's external and internal anatomical shape and size within the three-dimensional volume.

For example, as shown in the embodiment illustrated in FIGS. 2 and 8-10, the medical device position notification system 100 can include three external detector devices 110 configured to triangulate and define the subject's upper external anatomy shape and size within the three-dimensional volume. This embodiment including three external detector devices 110 can be beneficial because each of the three external detector devices 110 can form one of three points in space in order to define a single plane, such as an X-Y plane. The determination of an X-Y plane can allow the determination of a distance in the Z-direction. Thus, using three external detector devices 110 can enable the determination of the three-dimensional volume. The three points defined by the three external detector devices 110 can thereby define the patient size and relative anatomical locations within the three-dimensional volume.

The memory 130 can store algorithms 132 defining a generally known pre-defined anthropometric relationship between external anatomy and the internal anatomy, e.g. organs within a subject's body. The processor 120 can execute these algorithms 132 to relate the subject's external anatomy, as detected by the external detector devices 110, to approximate the shape and size of the internal organs associated with that external anatomy. In the embodiment illustrated in FIG. 2, the upper external anatomy shape and size can be used to calculate the shape and size of the lungs, esophagus and stomach. The memory 130 can further store image processing algorithms which the processor 120 can execute in order to visually render a graphical representation of the shapes of the lungs 12 and 14, esophagus 22 and stomach 24 in approximate size and location within the three-dimensional volume and depict the rendered graphical representation of the internal anatomy to scale on a suitable monitor or display 140. Thus, the medical device position notification system 100 can render a graphical representation of the subject's internal anatomy prior to or during insertion of the invasive medical device 200 to enable the accurate placement of the invasive medical device 200 in the proper location within the body.

As shown in FIGS. 1-2, the external position detector(s) 110 can be associated with a position detector, e.g., signal generator 222, of the medical device 200 in order to determine the relative position of the medical device 200.

Figure 5:
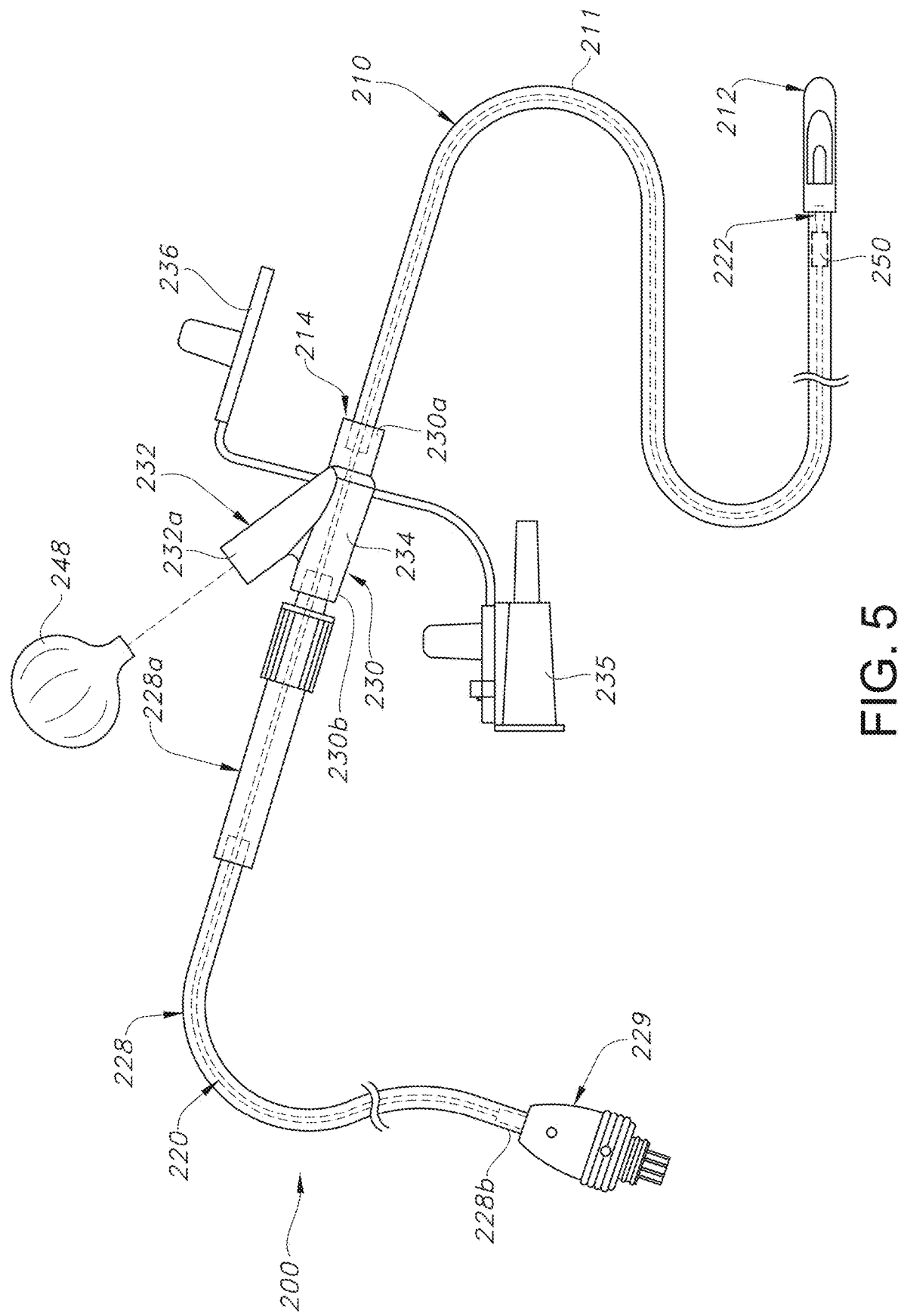
FIG. 5 illustrates a perspective view of a medical device in the form of an enteral catheter according to various embodiments of the present invention.

Turning now to FIGS. 2 and 5-10, the medical device 200 can include a catheter, such as an enteral feeding tube 210. The enteral feeding tube 210 extends from a distal end 212 to a proximal end 214 and can be connected to a distal end 230a of a connector 230 at the proximal end 214. The medical device 200 can additionally include a tubing assembly 228 configured to house at least a portion of a position detector signal generator assembly 220. A distal end 228a of the tubing assembly 228 can connect to a proximal end 230b of the connector 230. For example, as shown in FIG. 5, the distal end 230a and proximal end 230b of the connector 230 can extend along a longitudinal axis with a lumen 234 extending therebetween. Both the distal end 230a and proximal end 230b of the connector 230 can contain openings in communication with the lumen 234 and configured to receive the feeding tube 210 and the tubing assembly 228, respectively. Optionally, the connector 230 can also include a cap or cover 235 configured to close the opening at the proximal end 230b of the connector 230. In addition, the connector 230 can include a Y-port 232 in communication with the lumen 234 and the opening at the distal end 230a. The Y-port 232 can additionally have a cap or cover 236 configured to close the opening at the proximal end 232a of the Y-port. The Y-port 232 can be configured to receive tubing or other suitable means for delivering enteral feeding fluid, medicine, or other fluids through the feeding tube 210.

Figure 6:
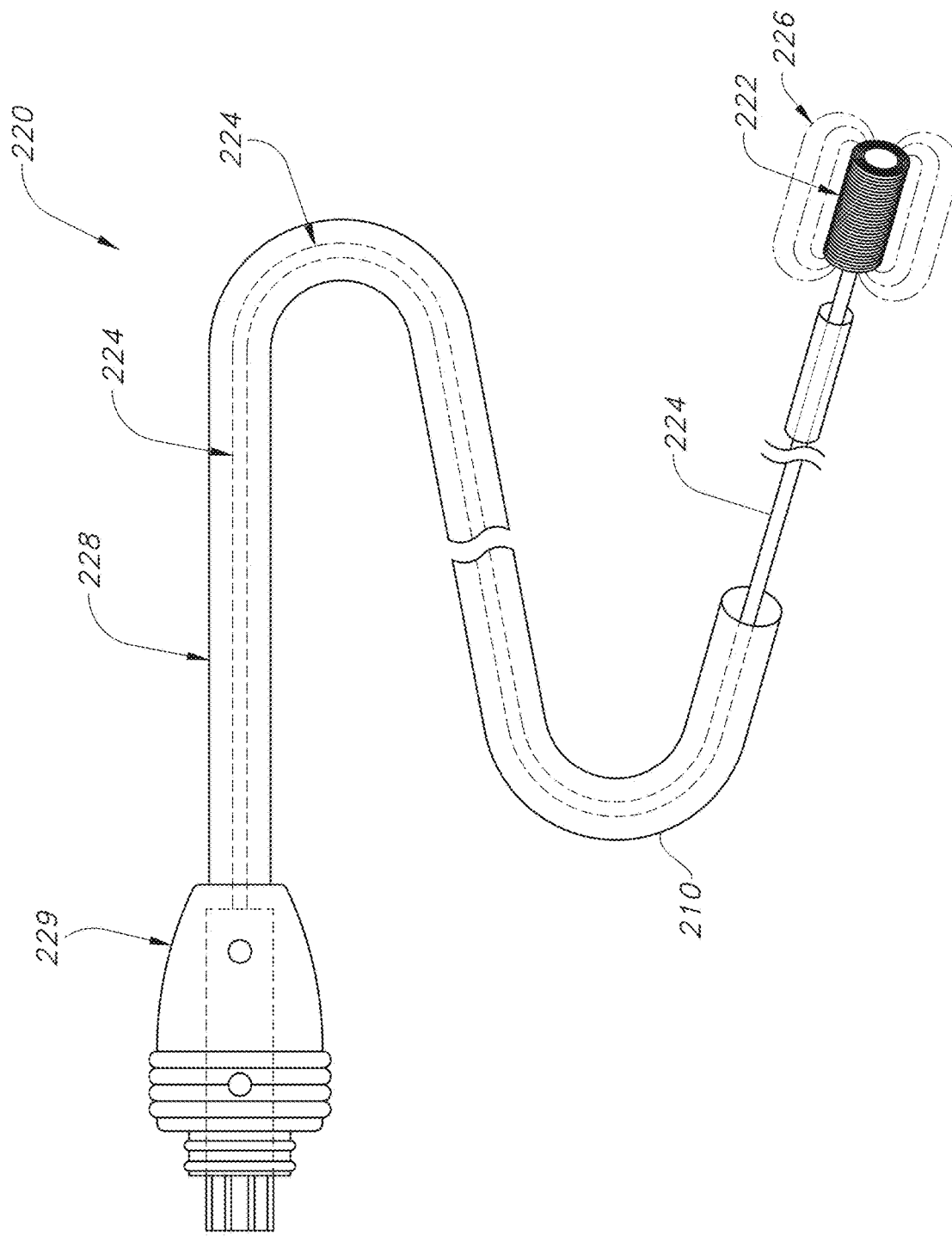
FIG. 6 illustrates a perspective view of a position detecting signal generator of the medical device of FIG. 5.

The position detector associated with the medical device 200 can be an electromagnetic field generator system 220, as shown in FIG. 6, including a wire assembly 224 comprised of one or more electrical wires and/or cables. The electrical wires and/or cables can be made of copper or any other suitable material. In one aspect, two wires and can be twisted around each other along the length of the wire assembly 224. Alternatively, the wire assembly 224 can include a coaxial cable, such as a micro coaxial cable, having an inner conducting wire surrounded by a tubular insulating layer, surrounded by a tubular conducting shield all sharing a geometric axis. In one aspect, not shown, the wire assembly 224 can additionally include an elongated stiffener to increase the rigidity of the wire assembly 224. The elongated stiffener can be made of steel, semi-rigid or rigid polymer, or any other suitable material. The configuration of the wire assembly 224 can be adapted to reduce any electromagnetic field surrounding the wire(s) along the length of the wire assembly 224. For example, in a twisted configuration, the electromagnetic forces of the twisted pair of wires counteract each other to reduce any electromagnetic field surrounding the wires, and in a configuration having a coaxial cable the conducting shield reduces the electromagnetic field surrounding the cable. Accordingly, the electromagnetic receivers 184 of the external position detectors 110 receive less, if any, signal interference from any electromagnetic fields generated by the wire assembly 224.

The proximal end of the wire assembly 224 can include a connector 229. The connector 229 can operatively connect the system 200 to the processor 120. In one embodiment, the connector 229 can electrically connect the system 220 to a power source of the processor 120. In another embodiment, the system 220 can include its own power source such as a battery.

As shown in FIG. 6, at a distal end of the wire assembly 224, the wires form a signal generator 222 having a coil configuration forming coils thereby producing a magnetic field generator as described below. The signal generator coil 222 is formed from a plurality of spirals produced by wrapping a portion of at least one electrical wire around itself. As an electrical current is transmitted through the wire(s) of the coil 222, the current travels in a circular path defined by the coils. This circular motion of current produced an electromagnetic field, B field or electromagnetic radiation 226. Although the embodiment illustrated includes coils, it should be appreciated that the signal generator 222 can include any alternate suitable mechanism or device which generates or produces magnetic energy, a magnetic field, or any other signal. In one embodiment, the magnetic field generator 222 includes a magnet such as a permanent magnet, resistive magnet or superconductive magnet.

In an alternative embodiment (not shown), the signal generator system 220 can be incorporated directly into the medical device 200, for example, by embedding the coil 222 and/or the wire assembly 224 into a wall 211 of a catheter tube 210.

In operation, when a power supply sends electrical current to the signal generator coils 222, and the coils transmit an electromagnetic field 226 capable of being detected by the receiver 184 of each external position detector 110, the receiver 184 of each of the external position detector(s) 110 detects the electromagnetic field 226 generated by the magnetic field signal generator coils 222 inside the human body. The processor 120 can cause the display device 140 to produce at least one representative image on the display device 140 which can assist a healthcare provider in a feeding tube placement procedure.

Figure 8:
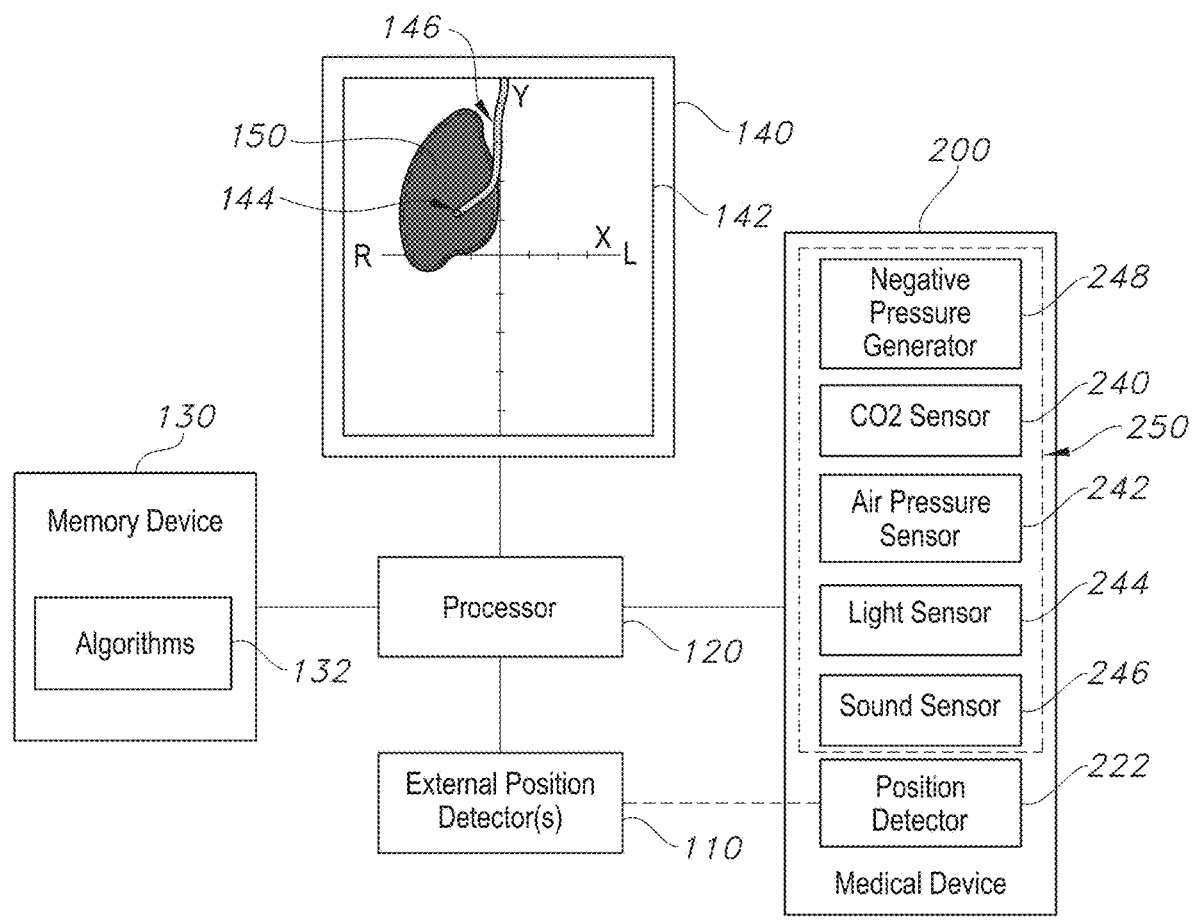
FIG. 8 illustrates a schematic view of the medical device position notification system of the present invention as the medical device deviates from the digestive tract into the respiratory tract, where a notification alert of the anatomical location of the medical device is displayed on the display device.
Figure 9:
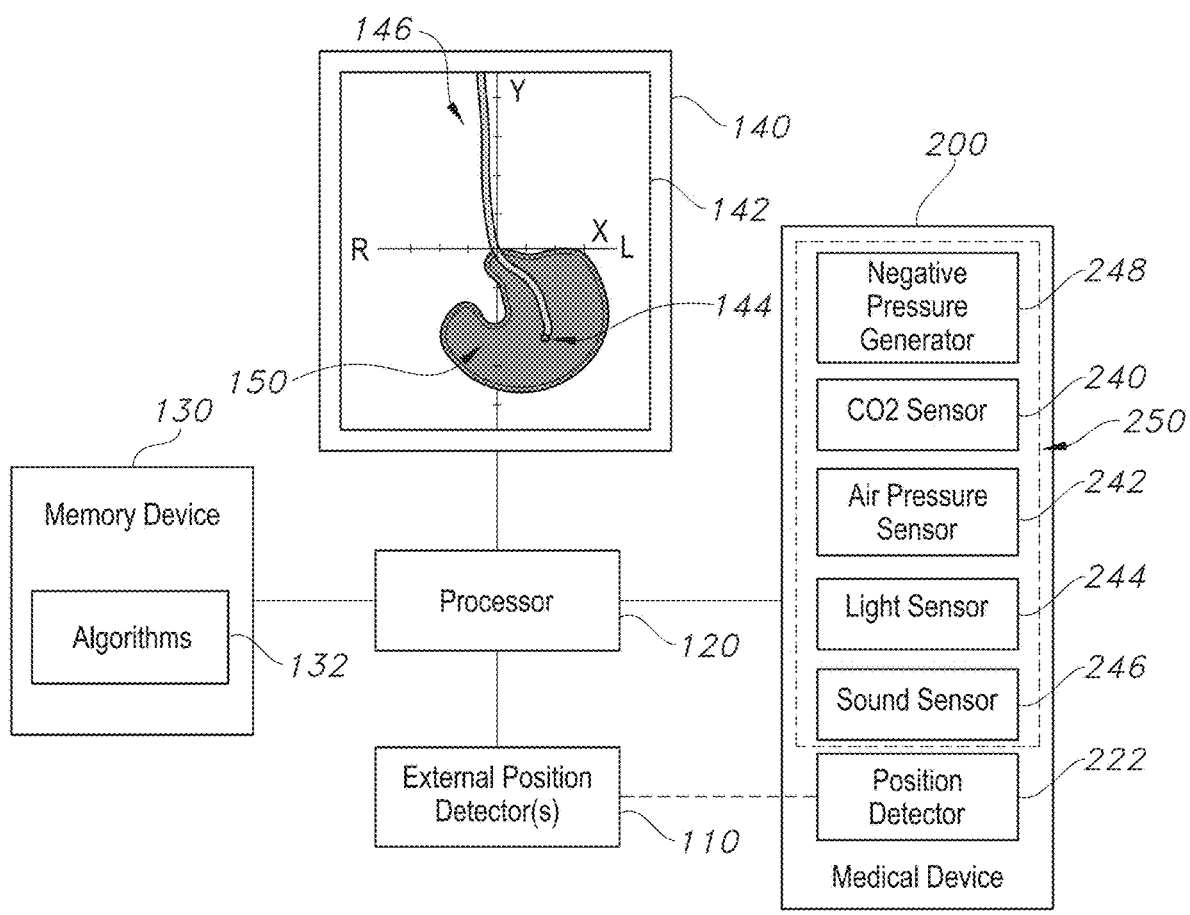
FIGS. 9 and 10 illustrate schematic views of the medical device position notification system of the present invention as the medical device reaches predetermined positions within the patient's digestive tract, where a notification of the anatomical location of the medical device is displayed on the display device.
Figure 10:
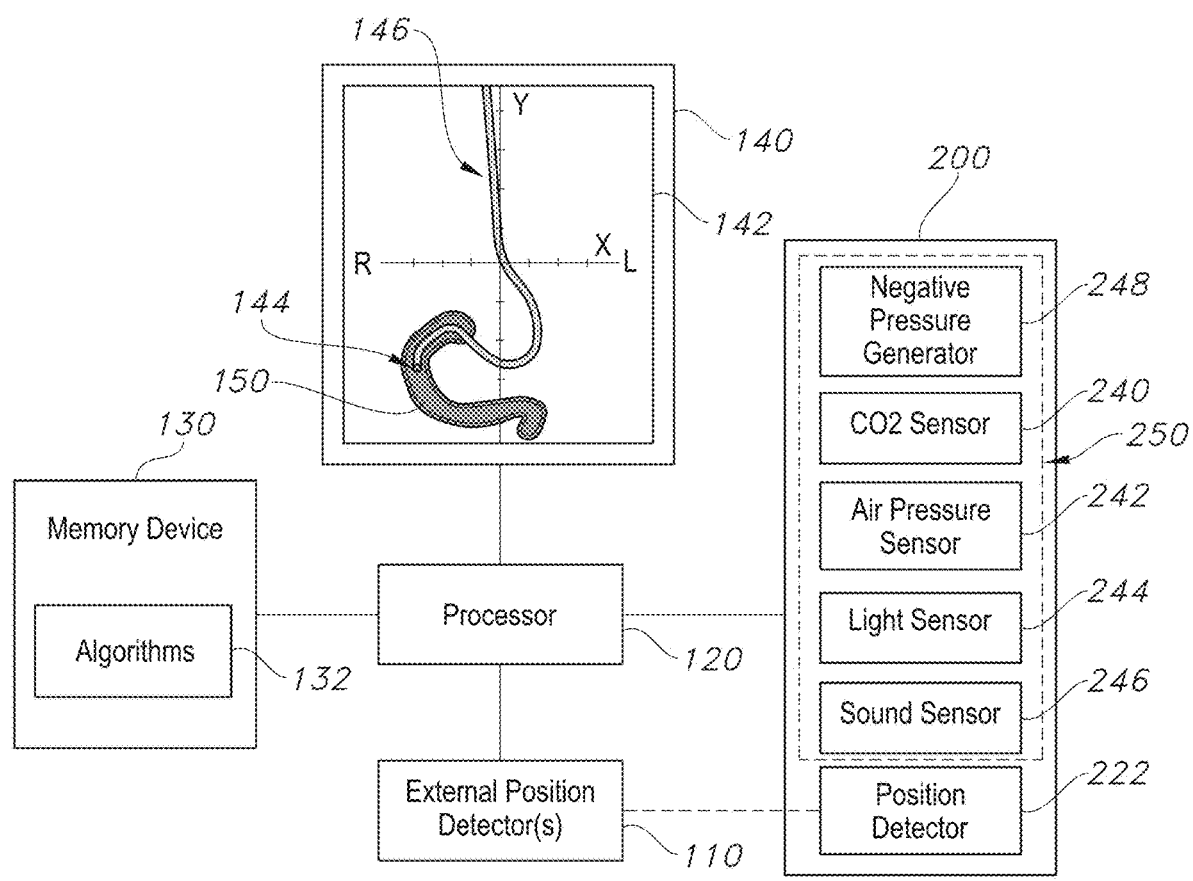

For instance, as illustrated in FIGS. 1-2 and 8-10, the system 100 having external position detectors 110 in operative communication with a signal generating position detector 222 of a medical device 200 can be used during placement of an enteral feeding tube 210 to monitor whether the catheter tube 210 follows a predetermined path through the digestive tract, e.g., esophagus 22, stomach 24 and small intestine 26, or if the tube deviates into the respiratory tract, e.g., trachea 28 or lungs 12 or 14. As shown in FIGS. 8-10, based on the signals sent to the processor 120 from the external position detectors 110 and the signal generator 222 of the medical device and the data and image processing performed by the processor 120 based on the algorithms 132 stored in the memory device 130, the display device 140 can display the current location 144 of the signal generator 222 of the medical device 200 in real-time on the display 142 along with a tracing path 146 of the signal generator 222 showing the path of movement of the catheter tube 210 through the patient's body 10. Further, as illustrated in the anatomical diagram shown in FIG. 2, the esophagus 22 is generally oriented in a vertical fashion along the midline of the body and does not deviate into the stomach 24 until a position that is generally below the xiphoid process 20. Thus, a deviation of the path of the tip 212 of the catheter tube 210 to the right or left of the midline of the patient above the xiphoid process 20 could indicate that the catheter tube 210 has deviated from the digestive tract and into the respiratory tract, e.g., the trachea 28 or one of the lungs 12 or 14. For instance, FIG. 8 shows the display device 140 showing a display 142 when the catheter tube 210 has deviated into the right lung 12. When the catheter tube 210 is positioned below the xiphoid process 20 and generally to the left side of the patient's body, it can indicate that the catheter tube 210 positioned in the stomach 24, as shown in FIG. 9. When the catheter tube 210 has proceeded a distance, e.g., a length of tubing, that is generally beyond the distance of the stomach based on the patient's anatomy size, it can indicate that the catheter tube 210 is positioned in the small intestine 26, as shown in FIG. 10.

Figure 7:
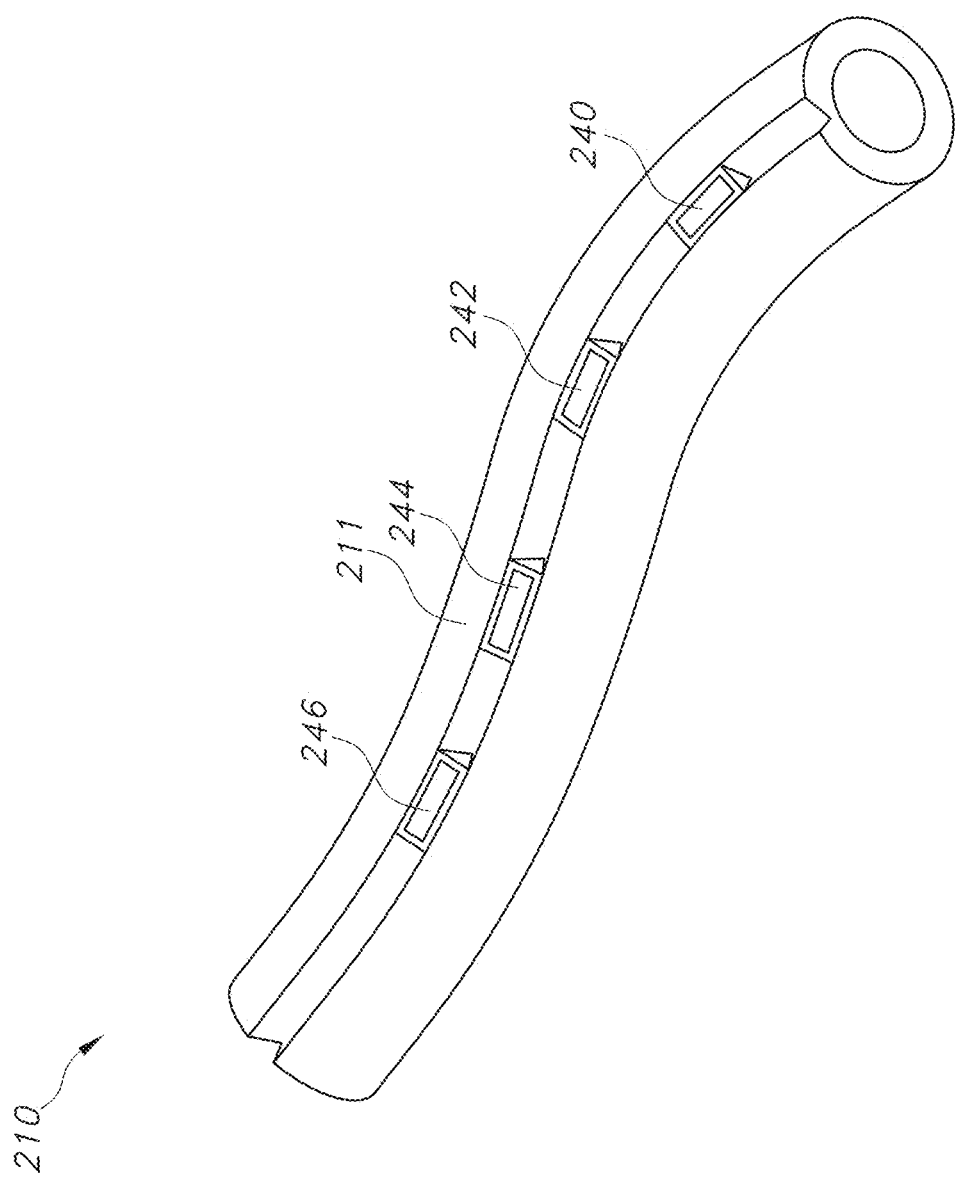
FIG. 7 illustrates a perspective view of an enteral catheter tube including various sensors according to embodiments of the medical device of FIG. 5.

As shown in FIG. 1, the medical device 200, e.g., enteral catheter tube 210 as described above, can further include additional sensors such as a carbon dioxide ($CO_2$) sensor 240, an air pressure sensor 242, a light sensor 244, a sound sensor 246, a vacuum decay sensor 248 in the form of a negative pressure generator, a humidity sensor, a temperature sensor, or combinations thereof. In one aspect, one or more sensor(s) can be embedded into the wall 211 of the catheter tube 210, as shown in FIG. 7. Additionally or alternatively, one or more sensor(s) can be disposed within the lumen of the catheter tube 210, e.g., as the signal generator 222 is shown in FIG. 6. Moreover, one or more sensor(s) can in some aspects be disposed at the proximal end 214 of the catheter tube 210, e.g., at the Y-port 232. When one or more of the sensor(s) described above are disposed within the lumen of the catheter tube 210 or embedded in the wall 211 of the catheter tube 210, the sensor(s) can be covered or surrounded by a filter 250 formed from a porous filter material or a porous filter media in order to prevent moisture from the opening in the distal tip 212 of the catheter tube 210 or from the patient's body cavity from contacting the sensor(s) and affecting any of the sensor measurements. For instance, the filter 250 can prevent water or other fluid ingress from contacting the sensor (s), while still allowing air to penetrate into the lumen. Turning now to the makeup of the filter 250, the filter contemplated by the present invention can allow gases but not liquids to pass therethrough. Stated alternately, the filter of the present invention can be vapor permeable and liquid impermeable. Exemplary suitable materials for the filter 250 include but are not limited to reticulated polymer foams, expanded polymers (such as Porex® expanded polymers available from Porex Corporation, having offices in Fairburn, Ga.), expanded PTFE (such as Gore-Tex® expanded PTFE available from W.L. Gore & Associates, Inc., having offices in Newark, Del.), and porous metals (or powdered metals). As will be appreciated, the rate at which the gases are allowed to pass through the filter 250 is not critical so long as it is sufficient to allow for a sufficient volume of air to come into contact with the sensor(s), e.g., for the carbon dioxide sensor 240, the air pressure sensor 242, the temperature sensor, and/or the humidity sensor, if present, to obtain accurate readings. It will also be appreciated that air flow rate may be affected or controlled in part by the composition of the filter 250. Nevertheless, in most embodiments, it is generally desirable for the insert to be able to allow at least 3 liters to 5 liters of gas to pass therethrough per hour. For use with a pediatric catheter, it may be desirable for the filter 250 in an appropriately sized adapter to be able to allow at least 1 liter to 2 liters of gas to pass therethrough per hour. Further, it will be appreciated that the filter 250 may be hydrophobic or hydrophilic, although it is desired that the insert or insert media be generally hydrophobic. Where the filter 250 is or contains a hydrophobic filter media or where the filter media is at least in part hydrophobically treated, the filter media may have larger pore sizes and therefore a higher flow rate therethrough (as compared to a hydrophilic or hydrophilically treated media) as the filter 250 will be less likely to absorb liquids, become saturated and allow liquid to pass therethrough.

Each of the sensor(s) can measure information related to the position of the medical device 200, e.g., catheter tube 210, within the patient 10 in order to determine or confirm a position of the medical device 200, as described in further detail below.

For example, the carbon dioxide sensor 240 can detect the partial pressure of $CO_2$ at the tip 212 of the catheter tube 210 within the passage traversed by the catheter tube 210 in order to detect whether the tip 212 is within the patient's airway or if it is continuing down a path of the digestive tract, i.e., the esophagus 22, stomach 24 or small intestine 26. Because the enteral catheter tube 210 has a known length, the $CO_2$ pattern (a waveform, as the $CO_2$ concentration rises and falls with the patient's respirations, typically three (3) to four (4) respirations per minute) determines if the tube 210 has deviated to the patient's airway. Stated differently, the amount or length of the enteral catheter tube 210 that has been inserted into the patient together with the $CO_2$ concentration detected by the sensor 240 convey to a health care provider whether the tip 212 is near the patient's airway and is possibly entering or disposed within the patient's airway rather than continuing down the pathway through the digestive tract, the intended destination of the tip 212. If the $CO_2$ concentration increases and/or continues to increase as the tube 210 is further inserted at a distance around or beyond that of the bifurcation zone of the esophagus 22 and the trachea 28, the signals sent by the sensor 240 to the processor 120 may be interpreted by the memory 130 as indicating that the distal tip 212 of the tube 210 is in or has entered the patient's airway. If, however, the $CO_2$ concentration does not increase or continue to increase past the bifurcation zone of the esophagus 22 and the trachea 28, the signals may be interpreted to indicate that the tube 210 is continuing within the digestive tract, i.e., on the correct pathway to the patient's stomach 24 or small intestine 26.

Similarly, the air pressure sensor 242 can detect the air pressure at the tip 212 of the catheter tube 210 within the passage traversed by the catheter tube 210 in order to detect whether the tip 212 is within the patient's airway or if it is continuing down a path of the digestive tract, i.e., the esophagus 22, stomach 24 or small intestine 26. Because the enteral catheter tube 210 has a known length, the air pressure pattern (a waveform, as the pressure rises and falls with the patient's respirations, typically three (3) to four (4) respirations per minute) determines if the tube 210 has deviated to the patient's airway. Stated differently, the amount or length of the enteral catheter tube 210 that has been inserted into the patient together with the pressure detected by the sensor 242 convey to a health care provider whether the tip 212 is near the patient's airway and is possibly entering or disposed within the patient's airway rather than continuing down the pathway through the digestive tract, the intended destination of the tip 212. If the air pressure maintains a waveform pattern as the tube 210 is further inserted at a distance around or beyond that of the bifurcation zone of the esophagus 22 and the trachea 28, the signals sent by the sensor 242 to the processor 120 may be interpreted by the memory 130 as indicating that the distal tip 212 of the tube 210 is in or has entered the patient's airway. If, however, the air pressure does not indicate a waveform pattern past the bifurcation zone of the esophagus 22 and the trachea 28, the signals may be interpreted to indicate that the tube 210 is continuing within the digestive tract, i.e., on the correct pathway to the patient's stomach 24 or small intestine 26.

In a similar manner, a sound sensor 246 can detect sound waves generated by air passing through an opening at the tip 212 of the catheter tube 210 within the passage traversed by the catheter tube 210 in order to detect whether the tip 212 is within the patient's airway or if it is continuing down a path of the digestive tract, i.e., the esophagus 22, stomach 24 or small intestine 26. For instance, the sound sensor 246 can be in the form of a microphone disposed at or near the distal tip 212 of the catheter tube 210. Sound data can be captured by the microphone 246 and signals of the sound data can be sent to the processor 120. Information stored in the memory 130, e.g., at least one algorithm 132, can be used to process the sound signals to remove unwanted noise and amplify frequencies of interest, e.g., known frequencies of respiratory sound. Thus, the information can be interpreted to determine if known sound frequencies of respiration are present, thus indicating whether the distal tip 212 of the catheter tube 210 is disposed in the airway. If the known sound frequencies of respiration are not found, the signals may be interpreted to indicate that the tube 210 is continuing within the digestive tract, i.e., on the correct pathway to the patient's stomach 24 or small intestine 26.

Additionally, the system 100 can include temperature and/or humidity sensors (not shown) disposed at or near the tip 212 of the catheter tube 210 to measure the temperature and/or relative humidity of the air near the tip 212 of the catheter tube 210. The temperature and/or humidity sensors can send signals to the processor 120 containing the measured temperature and/or relative humidity data. A constant temperature profile, a constant relative humidity profile, or both a constant temperature profile and a constant relative humidity profile communicated to the processor 120 after a predetermined amount of time indicates placement of the catheter tube 210 in the digestive tract (e.g., esophagus 22, stomach 24, intestine 26, or other anatomical region of the digestive tract of a patient. On the other hand, a non-constant or variable (e.g., sinusoidal wave, square wave, etc.) profile communicated to the processor 120 after a pre-determined amount of time indicates placement of the catheter tube 210 in the respiratory tract (e.g., trachea 28 or lungs 12 or 14).

In addition, a pH sensor can be used with the medical device 200 to differentiate whether the distal tip 212 of the medical device 200 is positioned in the respiratory tract or the digestive tract, and moreover, to differentiate or confirm where in the digestive tract the tip 212 may be (e.g., esophagus 22, stomach 24 or small intestine 26). The respiratory tract (e.g., trachea 28 and lungs 12 and 14) generally maintains a pH at or near the pH of blood, which is typically between about 7.38 to about 7.42. In contrast, a normal pH of the esophagus 22 is generally around 7.0, although the pH in the esophagus 22 can fluctuate lower during periods of reflux, i.e., when stomach acid enters the esophagus. The pH within the stomach 24 is generally between about 1.5 to about 4.0 due to the low pH of gastric acid, which is generally from about 1.5 to about 3.5. The pH in the small intestine 26 is higher than that of the stomach 24, generally from a pH of about 6.0 in the duodenum (i.e., immediately adjacent to the stomach 24) gradually increasing to a pH of about 7.4 at the terminal ileum of the small intestine 26. Because the enteral catheter tube 210 has a known length, the pH determines if the tube 210 has deviated to the patient's airway. Stated differently, the amount or length of the enteral catheter tube 210 that has been inserted into the patient together with the $CO_2$ concentration detected by the sensor 240 convey to a health care provider whether the tip 212 is near the patient's airway and is possibly entering or disposed within the patient's airway rather than continuing down the pathway through the digestive tract, the intended destination of the tip 212.

A light sensor 244 can also be used with the medical device 200 to differentiate whether the distal tip 212 of the catheter tube 210 of medical device 200 is positioned in the respiratory tract or the digestive tract. Due to the structural differences between the organs of the digestive tract, e.g., the esophagus 22, stomach 24 and/or small intestine 26, and those of the respiratory tract, e.g., trachea 28 and/or lungs 12 and 14, the amount of light reflectance with each organ differs. In general, more light is reflected from a light source to a light sensor when the light source is directly up against or very close to body tissue as in the digestive tract, whereas less light is reflected from a light source to a light sensor when the light source is in a more open environment such as the respiratory organs. In one aspect, the light sensor 244 can be formed from two fiber optic cables extending from a light and/or power source, e.g., a light box, to the distal tip 212 of the catheter tube 210, where the first fiber optic cable is connected to a light box. The light box transmits light through the first fiber optic cable to the distal tip 212 of the catheter tube 210, shown as light sensor 244 in FIG. 7. The second fiber optic cable runs alongside the first fiber optic cable and terminates at light sensor 244. When light is shined through the first fiber optic cable, it may be reflected off of the body tissue within the patient's body. The amount of light absorbed by the second fiber optic cable adjacent to the first fiber optic cable within the distal tip 212 of the catheter tube 210 is measured and sent to the processor 120. When the transmitted light is immediately reflected and returned by the second fiber optic cable, it may indicate that the distal tip 212 is disposed in the digestive tract, e.g., esophagus 22, and is on the correct pathway to the patient's stomach 24 or small intestine 26. In contrast, when the transmitted light is not immediately returned and/or the light reflected into the second fiber optic cable is weak, it may indicate that the distal tip 212 is disposed within the trachea 28 or lungs 12 or 14 and that the tube 210 needs to be repositioned. Moreover, differences in the amount or strength of light reflectance may further differentiate between positioning of the distal tip 212 of the catheter tube 210 between the esophagus 22, the stomach 24, and the small intestine 26.

In addition, a vacuum decay sensor 248 in the form of a negative pressure generator can be used with the medical device 200 to differentiate whether the distal tip 212 of the medical device 200 is positioned in the respiratory tract or the digestive tract. Because the esophagus 22 contains no significant structure support, it may readily collapse when negative pressure is applied. Conversely, the trachea 28 is lined with semi-rigid cartilage that maintains patency in the airway, even under moderate negative pressure. Thus, a vacuum decay sensor 248 in the form of a negative pressure generator can be used to apply a negative pressure through the catheter tube 210 during placement in order to differentiate the location of the distal tip 212 of the tube 210 based on this anatomical difference. For instance, the negative pressure generator of the vacuum decay sensor 248 can be a syringe bulb as shown in FIG. 5, a syringe, an aspiration tube, or any other suitable vacuum generator, connected to an access port of the tube 210, e.g., at the Y-port 232. In other aspects, the negative pressure generator 248 can be connected directly to the catheter tube 210. The negative pressure generator 248, e.g., syringe bulb as shown in FIG. 5, can be compressed and then released, either manually or mechanically, to create negative pressure within the catheter tube 210. The location confirmation can be made as follows:

if the bulb does not re-inflate, the tube tip 212 is in the esophagus 22 and the placement can continue through the digestive tract, but 2) if the bulb does re-inflate, the tube tip 212 is in the airway, e.g., trachea 28, and the tube 210 should be repositioned. As shown in FIG. 5, the negative pressure generator 248 can be manually compressed and observed by a health care provider to determine the vacuum decay, and thus the position, of the medical device 200. In other aspects, not shown, the negative pressure generator 248 may be electrically connected to the processor 120 and mechanically controlled to generate a negative pressure within the tube 210 and detect, e.g., using an air pressure sensor 242, whether the vacuum within the tube 210 decays, and then send signals with information about the vacuum decay to the processor 120 to be interpreted and displayed on the display device 140.

In some aspects of the invention, the $CO_2$ sensor 240 and the vacuum decay sensor 248, e.g., negative pressure generator, may be combined into a single unit configured to generate a negative pressure at the distal tip 212 of the catheter tube 210. Such a combined unit can be used in order to generate a vacuum necessary to collect air to determine the presence of $CO_2$ near the distal tip 212 of the catheter tube 210.

In use, the signals from the one or more sensors described above can be used to determine whether an inserted medical device 200 has reached a predetermined position within the patient's body, and/or whether the medical device 200 has deviated from the digestive tract of the patient, based on the interpretation of the signals communicated by the one or more sensors. Then, the system 100 can generate a notification, such as a notification displayed on the display device 140, regarding the position of the medical device 200 in the patient's body. The notification can indicate whether the medical device 200 has deviated from a predetermined path, such as the digestive tract. For instance, a warning notification can be displayed on the display device 140 as an alert to the health care provider. Additionally or alternatively, the notification can indicate when the medical device 200 has reached a predetermined position within the patient's body, such as by providing a confirmation notification.

As described above and shown in FIGS. 1-2 and 8-10, the signals sent to the processor 120 from the external position detector(s) 110 and the signal generating position detector 222 of the medical device 200 can be interpreted by the processor 120 using information, e.g., algorithms 132, stored in the memory device 130. The processor 120 can further conduct image processing using the information stored in the memory device 130 in order to instruct the display device 140 to generate a display 142 showing the current location 144 of the signal generator 222 of the medical device 200 in real-time along with a tracing path 146 of the signal generator 222 showing the path of movement of the medical device 200 through the patient's body. It is generally understood that the human eye can perceive a lag time of about 200 milliseconds or greater as a time delay. Put another way, the tracing path 146 shown on the display 142 represents the current location 144 of the signal generator 222 of the medical device 200 accurate to within about 300 milliseconds, such as within about 200 milliseconds, for example within about 150 milliseconds, such that the display 142 shows the current location 144 and the tracing path 146 without substantial, e.g., perceivable, lag time during insertion and/or positioning of the medical device 200. For example, the current location 144 can be shown in the display 142 in a first distinct color, if the display device 140 is capable of generating a color display 142, or with a first pattern, shading or brightness level. For example, as shown in FIGS. 8-10, the current location 144 can be depicted as a bright green dot. The tracing path 146 can be shown in a different color from the current location 144, or in the same color of the current location 144, or alternatively, the tracing path 146 can be shown with a less bright or more shaded depiction as compared to the current location 144. For example, as shown in FIGS. 8-10, the tracing path 146 can be shown as a light yellow line having a lower brightness than the bright green dot of the current location 144.

Additionally, as shown in FIGS. 8-10, the display device 140 is configured to show at least one notification 150 on the display 142 relating to the position of the medical device 200 within the patient's body. The notification 150 can be in the form of a visual symbol, for instance, a visual symbol of a bodily organ in which the medical device 200 is interpreted to be disposed. In other aspect, the visual symbol 150 can be a light-up shape in the general anatomical area of a bodily organ in which the medical device 200 is interpreted to be disposed. The shape can be any suitable shape, including but not limited to a circle, rectangle, triangle, star, trapezoid, or any other suitable shape. The visual symbol can also be a graphical image such as an exclamation point (!), a warning sign (Ø or X), a check mark (✓), or any other graphical image that is generally interpreted to depict either a warning or a confirmation.

For example, the display device 140 can generate a notification 150 that is intended to be a warning or alert when at least one sensor associated with the medical device 200 indicates that the medical device 200 has deviated from the predetermined path, e.g., into the respiratory tract instead of the digestive tract as described above and as shown in FIG. 8. The warning or alert notification can be in a first warning color, e.g., orange, red, yellow, or any other color that is suitably bright to be interpreted as a warning, when at least one sensor indicates that the medical device 200 has deviated from the predetermined path.

Moreover, when the at least one sensor indicates a deviation from the path, e.g., the position detector signal generator 222 together with the external position detectors 110 indicates that the medical device 200 has deviated to the right or left of the midline of the patient above the xiphoid process 20, as shown in FIGS. 2 and 8, the algorithms 132 stored in the memory device 130 can instruct the processor 120 to collect signals from one or more additional sensors, e.g., a $CO_2$ sensor 240, air pressure sensor 242, light sensor 244, sound sensor 246, vacuum decay sensor 248, temperature sensor, humidity sensor, and/or pH sensor as described above, to send additional information that may confirm the position of the medical device 200 within the patient's body. When at least a second sensor indicates that the medical device 200 has deviated from the path, e.g., is disposed in the respiratory tract, the warning notification symbol 150 can change from the first warning color to a second warning color, e.g., bright red or any other suitable warning color, begin flashing, or both. If a certain period of time passes and the medical device 200 is still interpreted as being in a position deviated from the path, additional warning notifications can be displayed on the display 142, such as additional color changes of the visual symbol 150, displaying of additional symbols, warning text, or other visible warnings.

Additionally, the display device 140 can show on the display 142 when the medical device 200 has reached a target predetermined position, based on the information collected by at least one or more of the sensors described above. For example, if the medical device 200, e.g., distal tip 212 of the catheter tube 210, is intended to read the patient's stomach 24, the display 42 can light up or show a visual symbol 150 in the shape of the patient's stomach 24 in a confirmation color, e.g., green or blue or any other suitable non-warning color, when the distal tip 212 of the medical device 200 has reached the stomach 24, as shown in FIG. 9. Similarly, as illustrated in FIG. 10, if the medical device 200 is intended to read the patient's small intestine 26, the display 42 can light up or show a visual symbol 150 in the shape of the patient's small intestine 26 or a portion thereof in a confirmation color, e.g., green or blue or any other suitable non-warning color, when the distal tip 212 of the medical device 200 has reached the small intestine 26. In particular, in some aspects, the information collected by the external position detector(s) 110 along with the light sensor 244, the vacuum decay sensor 248, and/or the pH sensor can be particularly useful to distinguish the positioning of the distal tip 212 of the catheter tube 210 between the esophagus 22, stomach 24 and small intestine 26. However, information collected from any of the sensors of the medical device 200 can contribute to the determination of whether the medical device 200 has reached the target predetermined position within the patient's body.

Although the above embodiments related to positioning an end or distal tip of a catheter, it should be appreciated that the medical device position notification system is operable to assist in the placement of any medical device or insertable component into a mammal in the course of stent placement, ablation, blockage removal, heat treatment, surgical procedure, fluid delivery or any other suitable invasive procedure. It should be appreciated that any type of catheter may be used for any of the medical procedures described above. It should also be appreciated that any suitable invasive or insertable medical device can be used in place of a catheter.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A medical device position notification system comprising:
   a processor;
   a memory device;
   a display device;
   a medical device configured to be inserted into a patient's body; and
   a first sensor and one or more second sensors associated with the medical device, wherein the first sensor comprises a position sensor and the one or more second sensors comprises a carbon dioxide sensor, a vacuum decay sensor, a light sensor, a sound sensor, a pressure sensor, a pH sensor, a humidity sensor, a temperature sensor, or a combination thereof;
   wherein the first sensor and the one or more second sensors are configured to measure and deliver signals containing information relating to a position of the medical device within a patient's body to the processor via an electrical connection;
   wherein the processor and the memory device are configured to interpret the signals sent by the first sensor to instruct the display device to generate a display of the position and a tracing path of the medical device;
   wherein the display of the position comprises a notification that is a visual symbol;
   wherein the processor is configured to interpret when the signals of the first sensor are indicating that the tracing path of the medical device has deviated from a digestive tract of the patient, further wherein the processor is configured to interpret the signals from the one or more second sensors to confirm the position of the medical device;
   wherein the display device is configured to display the notification in a first warning color if the first sensor indicates that the medical device has deviated from a predetermined path;
   wherein the processor and memory device are configured to modify the display on the display device to display the notification changing from the first warning color to a second warning color if at least one of the one or more second sensors confirms the first sensor indication that the medical device has deviated from the predetermined path.

2. The medical device position notification system of claim 1, wherein the processor and the memory device are configured to interpret the signals sent by the first sensor to instruct the display device to generate the display of the position and the tracing path of the medical device in real-time.

3. The medical device position notification system of claim 1, wherein the visual symbol is in a shape of an organ.

4. The medical device position notification system of claim 1, wherein the visual symbol displayed on the display device is a flashing visual symbol.

5. The medical device position notification system of claim 1, wherein the notification is displayed in a first confirmation color when the signals from the first sensor indicate that the medical device has reached a predetermined position or when the position of the medical device deviates from the predetermined path.

6. The medical device position notification system of claim 1, wherein the predetermined path is along a midline of the patient.

7. A method for medical device position guidance comprising:
   providing a medical device configured to be inserted into a patient's body and a first sensor and one or more second sensors associated with the medical device, wherein the first sensor comprises a position sensor and the second sensor comprises a carbon dioxide sensor, a vacuum decay sensor, a light sensor, a sound sensor, a pressure sensor, a pH sensor, a humidity sensor, a temperature sensor, or a combination thereof;
   inserting the medical device into an orifice of the patient's body;
   electrically connecting the first sensor and the one or more second sensors to a processor via a wired connection or a wireless connection;
   activating the first sensor and the one or more second sensors, wherein the first sensor measures information relating to a position of the medical device within a patient's body and sends signals containing the information relating to the position of the medical device within the patient's body to the processor via the wired or wireless electrical connection, wherein a display device is coupled to the processor and displays the position of the medical device within the patient's body, wherein the information relating to the position of the medical device comprises a tracing path of the medical device, wherein the processor and a memory device are configured to interpret the signals sent by the first sensor to instruct the display device to generate a display of the position and the tracing path of the medical device;

providing signals from the one or more second sensors to the processor;

interpreting, via the processor, the signals from the first sensor to indicate that the tracing path of the medical device has deviated from a digestive tract of the patient;

interpreting, via the processor, the signals from the one or more second sensors to confirm the position of the medical device;

displaying a notification in a first warning color when the first sensor indicates that the medical device has deviated from a predetermined path; and changing the notification on the display device from the first warning color to a second warning color upon at least one of the one or more second sensors confirming the first sensor indication that the medical device has deviated from the predetermined path.

8. The method of claim 7, wherein the first sends the signals containing the information relating to the position of the medical device within the patient's body to the processor in real-time.

9. The method of claim 7, wherein the display device generates the display of the position and the tracing path of the medical device in real-time.

10. The method of claim 7 further comprising:
advancing the medical device inside the body in a direction away from the orifice while the first sensor and the one or more second sensors are activated; and
observing the position of the medical device within the patient's body on the display device.

11. The method of claim 7 further comprising:
displaying a depiction of the position of the medical device within the patient's body on the display device.

12. The method of claim 7, wherein the notification displayed on the display device is a visual symbol.

13. The method of claim 12, wherein the visual symbol is in a shape of an organ.

14. The method of claim 12, wherein the visual symbol displayed on the display device is a flashing visual symbol.

15. The method of claim 12, wherein the visual symbol is displayed in a first confirmation color upon the first sensor and the one or more second sensors indicating that the medical device has reached a predetermined position.

16. The method of claim 7, wherein the predetermined path is along a midline of the patient.

17. The method of claim 7, wherein the orifice is a nose or a mouth.

18. A medical device position notification system comprising:
a processor;
a memory device;
a display device;
a medical device configured to be inserted into a patient's body; and
a first sensor and one or more second sensors associated with the medical device, wherein the first sensor comprises a position sensor and the one or more second sensors comprises a carbon dioxide sensor, a vacuum decay sensor, a light sensor, a sound sensor, a pressure sensor, a pH sensor, a humidity sensor, a temperature sensor, or a combination thereof;
wherein the first sensor and the one or more second sensors are configured to measure and deliver signals containing information relating to a position of the medical device within a patient's body to the processor via an electrical connection;
wherein the processor and the memory device are configured to interpret the signals sent by the first sensor to instruct the display device to generate a display of the position of the medical device;
wherein the display of the position comprises a notification that is a visual symbol;
wherein the processor is configured to interpret when the signals of the first sensor are indicating that the medical device has deviated from a digestive tract of the patient, further wherein the processor is configured to interpret the signals from the one or more second sensors to confirm the position of the medical device;
wherein the display device is configured to display the notification of a first warning if the first sensor indicates that the medical device has deviated from a predetermined path;
wherein the processor and memory device are configured to modify the display on the display device to display the notification changing from the first warning to a second warning if at least one of the one or more second sensors confirms the first sensor indication that the medical device has deviated from the predetermined path.

19. The medical device position notification system of claim 18, wherein the second warning is a flashing first warning.

* * * * *

UNITED STATES PATENT AND TRADEMARK OFFICE
CERTIFICATE OF CORRECTION

| | | |
|---|---|---|
| PATENT NO. | : 12,426,960 B2 | Page 1 of 1 |
| APPLICATION NO. | : 18/661830 | |
| DATED | : September 30, 2025 | |
| INVENTOR(S) | : Donald McMichael et al. | |

It is certified that error appears in the above-identified patent and that said Letters Patent is hereby corrected as shown below:

In the Claims

Column 21, Claim 8, Line 25, reading:
The method of claim 7, wherein the first sends the Should Read:
The method of claim 7, wherein the first sensor sends the Signed and Sealed this
Ninth Day of December, 2025

John A. Squires
*Director of the United States Patent and Trademark Office*